(12) United States Patent
Hrboticka

(10) Patent No.: US 8,496,880 B2
(45) Date of Patent: Jul. 30, 2013

(54) TEST STRIP CONSTRUCTION

(75) Inventor: Eva Hrboticka, Brno (CZ)

(73) Assignee: Precision Laboratories, Inc., Cottonwood, AZ (US)

( * ) Notice: Subject to any disclaimer, the term of this patent is extended or adjusted under 35 U.S.C. 154(b) by 60 days.

(21) Appl. No.: 13/078,222

(22) Filed: Apr. 1, 2011

(65) Prior Publication Data

US 2012/0251409 A1 Oct. 4, 2012

(51) Int. Cl.
*G01J 1/48* (2006.01)

(52) U.S. Cl.
USPC .......................................................... 422/87

(58) Field of Classification Search
USPC .......................................................... 422/87
See application file for complete search history.

(56) References Cited

U.S. PATENT DOCUMENTS 4,540,408 A * 9/1985 Lloyd ............................. 604/294
2003/0225381 A1 * 12/2003 Van Dalen ..................... 604/294

* cited by examiner

*Primary Examiner* — Lore Jarrett
(74) *Attorney, Agent, or Firm* — Ladas & Parry LLP

(57) ABSTRACT

A test strip construction includes a test strip having a testing region bearing a chromogenic reagent to detect the presence of a substance in a fluid test sample. A supporting member is attached to one end of the test strip in a manner such that the testing region is remote form the attachment point and is free from any contact with supporting member. When dipped into the test sample the test strip can flutter away from the supporting member to allow for full contact between that the testing region and the test sample. When removed from the test sample the supporting member provides a consistent background for observation of color changes of the reagent.

7 Claims, 2 Drawing Sheets

TEST STRIP CONSTRUCTION

FIELD OF THE INVENTION

This invention relates generally to test strips, and particularly to test strips that utilize chromogenic indicators.

BACKGROUND OF THE INVENTION

Test strips are widely used diagnostic testing devices to detect the presence of one or more substances in a fluid test sample, and have applicability in the medical field as well as in chemical and industrial fields. Test strips are typically of an adsorbent material for receiving the test sample. The adsorbent material matrix serves as a carrier for an appropriate reagent for detecting the presence of the substance to be monitored. When the test sample is adsorbed onto the testing region, the reagent reacts with the substance in the test solution to indicate its presence. Chromogenic reagents are commonly used so that a visible change in color in the testing region of the strip resulting from the desired reaction confirms the presence of the monitored substance. The lack of a reaction by the reactant when the testing sample is within the test region indicates the absence of the substance.

While chromogenic test strips can be held at one end by the user and dipped to some degree into the test solution, or put on a try or the like and the test solution deposited on the strip such as by a dropper, such a construction and technique are subject to what can be called the chromatography effect, where the test solution migrates through capillary action through the portion of the test strip not initially wetted, and carries with it the developed color product, diluting and washing out the color effect. Particularly at low concentration levels, where small color changes are to be expected, the washout effect can render the test useless.

Accordingly, common test strip constructions attach the test strip to a backing, typically in the shape of a paddle, to allow the test strip to be more easily handled and the entire test strip to be dipped into the solution to be tested, and to provide structural support for the adsorbent material. The backing material usually comprises an impermeable, semi-rigid material that underlies the entirety of the absorbent material and typically extends past the adsorbent material to form a gripping element body for conveniently holding the test strip material. The backing material is adhesively attached to the adsorbent material.

While such prior art test strip paddle constructions are reliable at high concentration levels of the substance to be tested for, a major disadvantage of such constructions is that the presence of the backing and/or the adhesive that attaches the backing to the adsorbent material can interfere with the activity of the reagent. When using known test strips on fluid samples which contain low levels of the substance sought to be detected, interference caused by the backing and/or its adhesive can cause the test strip to show a "false negative" by failing to show a positive reaction indicating the presence of a substance. Therefore, it is desired to have a test strip construction that can avoid the potential for interaction between the test strip an its reagents and the supporting member or adhesive.

Another disadvantage of many prior test strips is that their design often prohibits a sufficient quantity of the test sample to react with the reagent for adequate testing results. When the test strip is backed, such a construction may inhibit sufficient adsorption of the test fluid, or result in uneven adsorption across the testing region. Striations may develop in the testing region, which makes it difficult to obtain a clear or consistent reading of the results.

Accordingly, it is an object of the present invention to provide an improved test strip construction of the supported type that avoids interaction between the supporting member and the testing region of the test strip.

Yet another object of the present invention is to provide an improved test strip construction that allows the testing region to be in full contact with the fluid to be tested.

It is another object of the present invention to provide a test strip that has improved accuracy, particularly for detecting substances at low concentration.

A further object of the present invention is to provide a test strip that is economical and efficient and cost effective to manufacture.

SUMMARY OF THE INVENTION

The foregoing objects are met by the present invention directed to an improved test strip construction. The test strip construction is fabricated out of an adsorbent material which is adapted to receive a fluid test sample. The test strip has a testing region that carries a reagent to detect the presence of a substance.

A supporting member is attached solely to one end of the test strip at a location remote from the testing region in a manner whereby substantially the entire testing region is free from any contact with the supporting member. The supporting member extends the length and width of the test strip, however, to provide a consistent background against which color changes in the test strip can be viewed. But for the affixed end of the test strip, the test strip and testing region have no backing or adhesive, which leads to improved and consistent adsorption of the fluid test sample as well as the activity of the reagent with the test sample as compared to test strips affixed to a backing. This results in improved accuracy of the test results, particularly at low concentrations of the substance to be tested.

The attachment of the supporting member to only one end of the test strip allows the test strip to move free of the supporting member for virtually its entire length. Thus the user can grasp the supporting member, dip the test strip into a fluid sample to be tested and, by gentle hand motion, cause the test strip to flutter in the test solution. This allows the test strip and testing region to fully and completely contact the test solution.

DESCRIPTION OF THE DRAWINGS

The above and other objects, features and advantages of the present invention will become apparent from the following description of a preferred but, nonetheless, illustrative embodiment of the invention, taken in conjunction with the accompanying drawings, wherein.

DETAILED DESCRIPTION OF PREFERRED EMBODIMENTS

Figure 1:
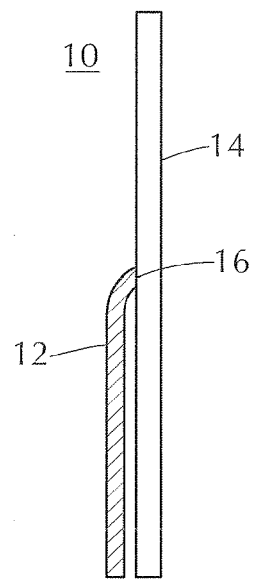
FIG. 1 provides a side elevational view of the improved test strip construction of the present invention.

With particular reference to the drawings, the present invention is directed to an improved test strip construction 10. The test strip construction 10 comprises a test strip 12 fabricated out of an adsorbent material, as known in the art. Materials suitable for the test strip include cotton, fiber, cellulose, or synthetic materials as generally known. As also known in the art, the test strip is impregnated with a reagent chosen to be reactive to the substance sought to be detected by the test strip construction. In addition to the reactive reagent, the test strip may also carry buffers, stabilizers, and other formulations, also as known in the art, to assist in providing a consistent and accurate response by the reagent to the tested-for substance. Preferably, the entirety of the test strip is treated with the appropriate formulations, and standard procedures may be used to carry out the treatment process. Typically, the reagent is chromogenic, which provides a color change upon reaction with the tested-for substance. Observation of the color change and comparison of the color to a set of standards indicates the presence of the substance, and often its concentration.

A supporting member 14 is attached to one end of the test strip 12. The supporting member 14 may be attached to the test strip by an adhesive or by other means known in the art. As shown in the figures, the supporting member 14 is preferably attached to one end of the testing strip 12 such that the supporting member backs the test strip for essentially the strip's full length. But for the point of attachment 16, substantially the entire test strip 12 is free from any fixed contact with the supporting member, although it can rest against the supporting member. The upper portion 18 of the supporting member, above the attachment point 16, serves as the handle for the test strip construction, and may be grasped by the user to hold the construction. The supporting member may be of any generally-recognized material, such as plastic or wood, and may be of any convenient size to facilitate attachment of the test strip and provision of a handle portion.

Figure 2:
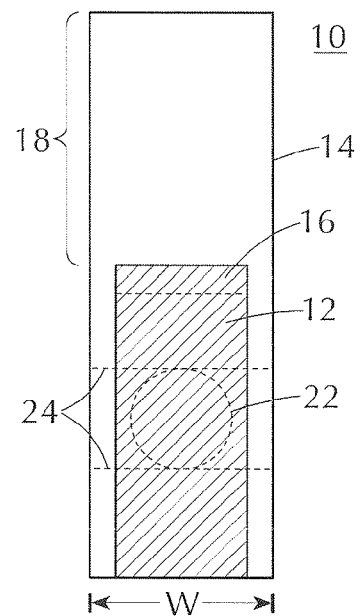
FIG. 2 provides a view of the improved test strip construction immersed in a fluid test sample in a container.

The attachment of the test strip 12 to the support member 14 solely at an end of the test strip 2 allows the majority of the test strip length to move independently of the supporting member. Thus, as depicted in FIG. 2, when the test strip construction is immersed into a solution 20 to be tested, with the test strip fully immersed and exposed to the solution, gentle motion by the user applied to the handle portion of the construction will allow the test strip to flutter, free from the supporting member, providing for intimate contact between the solution and all surfaces of the test strip save for the small portion of the strip attached to support member at 16. This insures full wetting of the strip and contact between the solution and the reagent and other constituents carried by the test strip. To insure that the test strip is fully exposed to the solution, the test strip must be chosen to minimize the likelihood of adhesion to the support member when in the solution. Blotting papers, such as Ahlstrom 319 or 8975 and Whatman 8S, have been found acceptable.

When the test strip construction is removed from the solution, the free-hanging portion of the strip will normally stick to the supporting member due to adhesive effects. At this point such adhesion is preferred, as it provides a consistent background to view color changes in the reagent and helps insure consistent sample-to-sample readings and comparison with known standard. Preferably, the supporting member is white or light-colored, to provide an unbiased background. When the supporting member is of a plastic formulation, the colorant may be easily added to the plastic compound. Alternatively, it may be applied to the surface of the supporting member by a painting, spraying or dipping process.

The provision of a substantial area of the test strip free of forced intimate contact with the supporting member insures that interference effects that otherwise can be present when the test strip is bonded or otherwise in contact with the supporting member during the dipping into the fluid to be tested and thereafter when the chromogenic reaction is occurring, while the presence of the supporting member behind the strip for viewing the reaction results facilitates the visual interpretation of the results and assists in maintaining uniformity of interpretation.

Figure 3:
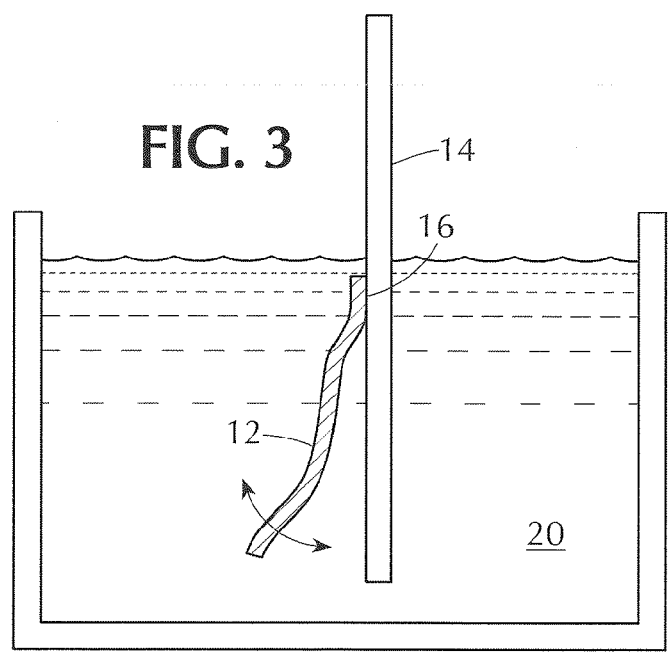
FIG. 3 is a front elevation view of the test strip construction.

To further insure that any effects of the presence of the attachment point, however slight are minimized, and to direct the user to observe the chromogenic effects at a region well displaced from the attachment point, visual markings may be provided, either on the test strip or on the supporting member, to delineate a chosen region of the test strip for observation purposes. The marking may be, for example, an embossed line 22 impressed into the test strip 1 as shown in FIG. 3, or analogous linage 24 which may be etched or painted on the surface of the supporting member 14 as likewise shown in the Figure. The width w of the supporting member may be incrementally larger than the width of the test strip 12 to provide easy reference for linage appearing at one or both of the side edges of the supporting member to be seen and referenced to the test strip.

Figure 4:
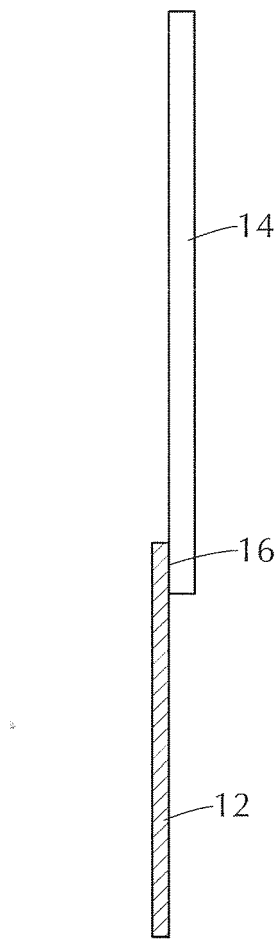
FIG. 4 is a side elevation view of an alternative embodiment of the invention.
Figure 5:
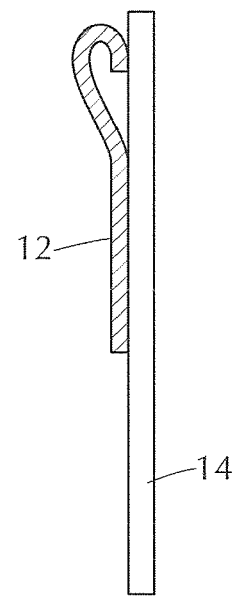
FIG. 5 is a side elevation view of the embodiment of FIG. 4 in position for visual analysis.

An alternative embodiment of the invention is depicted in FIGS. 4 and 5. As shown in FIG. 4, the test strip 12 is attached to the supporting member 14 at the distal end of the supporting member, whereby in use the test strip hangs down below the supporting member for dipping into the solution to be tested. When the test strip is removed from the solution the supporting member is rotated such that the test strip folds over the attachment point to lie upon the adjacent portion of the supporting member for the visual inspection.

It should be understood, of course, that the specific forms of the invention herein illustrated and described are intended to be representative only, as certain changes may be made therein without departing from the clear teachings of the disclosure. Accordingly, reference should be made to the following appended claims in determining the full scope of the invention.

What is claimed is:

1. A test strip construction especially adapted for detecting low levels of a substance in a fluid test sample into which the construction is immersed and then removed for visual analysis thereof, comprising:
   a test strip comprising an adsorbent material having a non-separable testing region therein bearing a reagent for the detection of the substance in the fluid test sample;
   an elongated supporting member attached to said test strip only at a point substantially at a first end of the test strip, a remainder portion of the test strip being free of the supporting member, the testing region being located on the remainder portion of the test strip;
   the supporting member having a first portion serving as a backing for the test strip and the testing region thereof when the testing region overlies the first portion for visual analysis of the testing region after immersion and removal from the fluid test sample and a second non-backing portion not backing the test strip and testing region adjacent the first portion serving as a handle for the construction.

2. The test strip construction of claim 1 wherein said supporting member is attached at the point to said test strip by an adhesive.

3. The test strip construction of claim 1 wherein said reagent is a chromogenic reagent.

4. The test strip construction of claim 1 wherein the supporting member first portion extends in a first direction from the attachment point and the second portion extends in an opposite direction.

5. The test strip construction of claim 1 wherein the attachment point is located at an end of the supporting member.

6. The test strip construction of claim 1 wherein at least one of the test strip and supporting member is provided with indicia to delineate the testing region.

7. The test strip of claim 6 wherein the indicia are provided at side edges of the supporting member and the supporting member has a width greater than a width of the test strip such that the indicia are not covered by the test strip.

* * * * *